United States Patent [19]

Wong

[11] Patent Number: 5,312,390
[45] Date of Patent: * May 17, 1994

[54] OSMOTIC DEVICE WITH DELAYED ACTIVATION OF DRUG DELIVERY

[75] Inventor: Patrick S.-L. Wong, Palo Alto, Calif.

[73] Assignee: Alza Corporation, Palo Alto, Calif.

[*] Notice: The portion of the term of this patent subsequent to Jun. 29, 2010 has been disclaimed.

[21] Appl. No.: 4,340

[22] Filed: Jan. 14, 1993

Related U.S. Application Data

[63] Continuation-in-part of Ser. No. 819,417, Jan. 10, 1992, Pat. No. 5,223,265.

[51] Int. Cl.⁵ .............................................. A61K 9/22
[52] U.S. Cl. ................................ 604/892.1; 424/453; 424/473
[58] Field of Search ............... 604/892.1, 890.1, 891.1; 424/453, 462, 463, 468, 471–474, 482

[56] References Cited

U.S. PATENT DOCUMENTS

| | | |
|---|---|---|
| 3,732,865 | 5/1973 | Higuchi et al. ............... 604/892.1 |
| 3,845,770 | 11/1974 | Theeuwes et al. . |
| 3,865,108 | 2/1975 | Hartop . |
| 3,916,899 | 11/1975 | Theeuwes et al. . |
| 3,995,631 | 12/1976 | Higuchi et al. . |
| 3,995,632 | 12/1976 | Nakano et al. ................ 128/260 |
| 4,002,173 | 1/1977 | Manning et al. . |
| 4,034,756 | 7/1977 | Higuchi et al. . |
| 4,063,064 | 12/1977 | Saunders et al. . |
| 4,088,864 | 5/1978 | Theeuwes et al. . |
| 4,111,202 | 9/1978 | Theeuwes . |
| 4,200,098 | 4/1980 | Ayer et al. . |
| 4,207,893 | 6/1980 | Michaels . |
| 4,265,874 | 5/1981 | Bonsen et al. . |
| 4,285,987 | 8/1981 | Ayer et al. ............... 427/3 |
| 4,320,759 | 3/1982 | Theeuwes . |
| 4,327,725 | 5/1982 | Cortese et al. . |
| 4,449,983 | 5/1984 | Cortese et al. . |
| 4,595,583 | 6/1986 | Eckenhoff et al. . |
| 4,601,896 | 7/1986 | Nugent ............... 424/36 |
| 4,612,008 | 9/1986 | Wong et al. . |
| 4,777,049 | 10/1988 | Magruder et al. ............ 424/457 |
| 4,872,873 | 10/1989 | Zingerman ............ 604/892.1 |
| 4,874,388 | 10/1989 | Wong et al. ............ 604/891.1 |
| 4,955,881 | 9/1990 | Eckenhoff ............ 604/890.1 |
| 5,017,381 | 5/1991 | Maruyama et al. ............ 424/472 |
| 5,023,088 | 6/1971 | Wong ............ 424/473 |
| 5,034,229 | 7/1991 | Magruder et al. ............ 424/422 |

FOREIGN PATENT DOCUMENTS 0384642 8/1990 European Pat. Off. ....... A61K 9/22

*Primary Examiner*—C. Fred Rosenbaum
*Assistant Examiner*—V. Alexander
*Attorney, Agent, or Firm*—Paul L. Sabatine; Jacqueline S. Larson; Jean M. Duvall

[57] ABSTRACT

The present invention is directed to a fluid-imbibing drug delivery device which is useful for the initial delayed delivery of an active agent formulation to a fluid environment of use, the initial delay period to startup or activation being of a predetermined length of time. The delivery of the agent formulation from the dispensing device, once begun, is continued over a predetermined prolonged period of time.

16 Claims, 2 Drawing Sheets

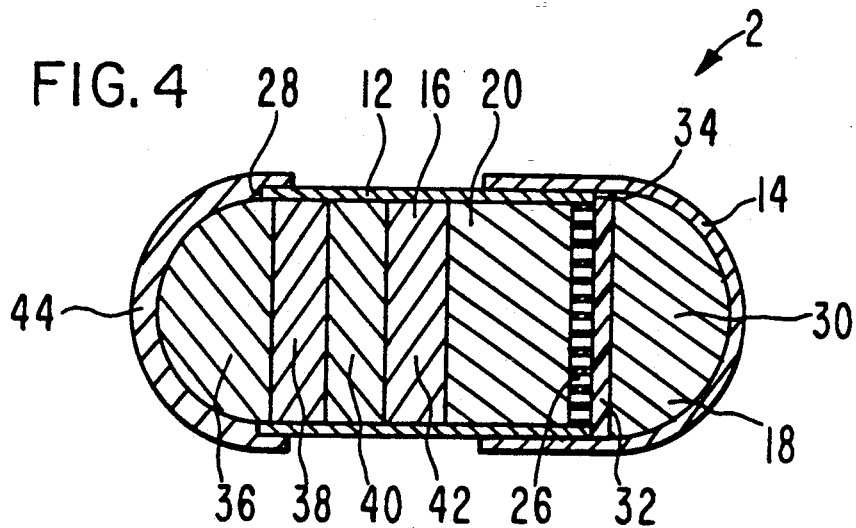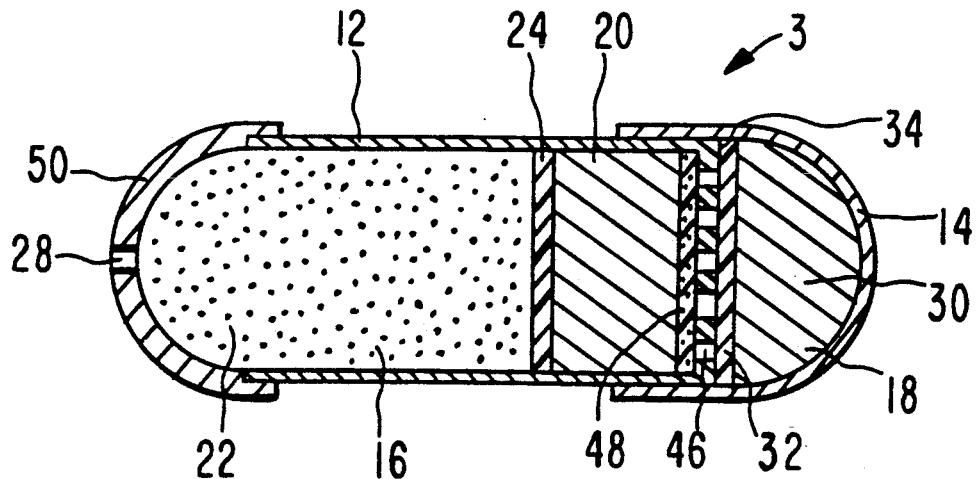

OSMOTIC DEVICE WITH DELAYED ACTIVATION OF DRUG DELIVERY

RELATED APPLICATION

This application is a continuation-in-part of U.S. application Ser. No. 07/819,417, filed on Jan. 10, 1992, now U.S. Pat. No. 5,223,265, issued Jun. 29, 1993.

FIELD OF THE INVENTION

The present invention is related to the delayed delivery of an active agent. More particularly, it is related to osmotically-activated devices for dispensing active agents to a biological environment of use following an initial delay.

BACKGROUND OF THE INVENTION

Osmotic dispensing devices for delivery of therapeutically active agents are well known in the art. Such devices use an expansion means to deliver an agent to an environment of use over a period of hours, days or months. The expansion means absorbs liquid, expands, and acts to drive out beneficial agent formulation from the interior of the device in a controlled, usually constant manner. The osmotic expansion means is used to controllably, usually relatively slowly, and over a period of time, deliver the agent. Because they become activated as soon as they are placed in a fluid environment, these devices are not generally used to delay the initial release of the agent. Where osmotic technology has been used to provide an initial delay, the delay is followed by the rapid release, or substantially simultaneous introduction, of all of the agent or all of the dosage form(s) containing the agent into the environment of use at one time. See, PCT publication WO 92/13521. This is not always an appropriate method of delivery, such as when delivery of an agent at a constant rate over a prolonged period of time is desired.

The delay of the initial release of an agent has primarily been previously effected by coating the agent or a formulation containing the agent with a dissolvable or bioerodible coating layer, such as gelatin or an enteric coating, which coating layer dissolves or erodes in the environment of use to then make the agent available. Delayed initial release has also been provided by dispersing the agent in a dissolvable or erodible matrix. However, such systems are often unreliable and release cannot be controlled with great accuracy due to the variability and relatively uncontrollable nature of erosion and dissolution.

Therefore, there remains a continuing need for improved methods and systems for providing a delayed activation and thus a delayed initial delivery of an active agent to an environment of use that are reliable and that can be programmed to deliver the agent after a particular interval with increased accuracy.

SUMMARY OF THE INVENTION

The present invention is directed to a fluid-imbibing dispensing device for the initially delayed delivery of an active agent to a fluid environment of use, followed by continuous delivery of the agent to the environment over a prolonged period of time. The delivery device of the invention is formed of a first housing and a second housing with an open end, the housings being in reversibly sliding telescoping arrangement with each other, which device maintains its integrity in the fluid environment; an active agent delivery chamber within the first housing for the continuous delivery of an active agent to the environment over a prolonged time period, the delivery chamber including at least one active agent formulation containing at least one active agent, an exit means for providing communication between the active agent formulation and the environment of use, a first expansion means for dispensing the active agent formulation through the exit means to the environment, and means for allowing passage of fluid into the first expansion means (the "fluid-passage means"); and an expansion chamber within the second housing for separating apart the first and second housings of the device after exposure to the environment of use to provide the initial delay, the expansion chamber including a second expansion means and a push plate.

The invention also is directed to a method for delaying the initial delivery of an active agent to a fluid environment of use, the method comprising placing the dispensing device of the invention into the environment of use, allowing fluid to be imbibed through at least a portion of the second housing of the dispensing device for causing the second expansion means to expand over time and exert pressure on the slidably connected first and second housings to push apart and separate the two housings of the device to expose the fluid-passage means of the first housing to the environment, and allowing fluid to be imbibed through the fluid-passage means for causing the first expansion means to expand to push the active agent formulation from the delivery device, thereby delivering the active agent into the environment of use.

DESCRIPTION OF THE DRAWINGS

The drawings are not drawn to scale, but are set forth to illustrate various embodiments of the invention. Like numbers refer to like structures.

FIG. 4 is a cross-sectional view of another embodiment of the delivery device of the present invention, the device being in closed or prepared form.

FIG. 5 is a cross-sectional view of yet another embodiment of the delivery device of the present invention, the device being in closed or prepared form.

DETAILED DESCRIPTION OF THE INVENTION

The present invention provides a device which is useful for the initial delayed delivery of an active agent formulation to a fluid environment of use, the initial delay period to startup or activation being of a predetermined length of time. The delivery of the agent formulation from the dispensing device, once begun, is continued over a predetermined prolonged period of time. By "prolonged period of time", as used herein, is meant an extended time period such as for about 1 hour up to about 48 hours.

The dispensing devices of the invention find use, for example, in humans or other animals. The environment of use is a fluid environment and can comprise the stomach, the intestinal tract, or a body cavity such as the peritoneum or vagina. A single dispensing device or several dispensing devices can be administered to a subject during a therapeutic program.

Figure 1:
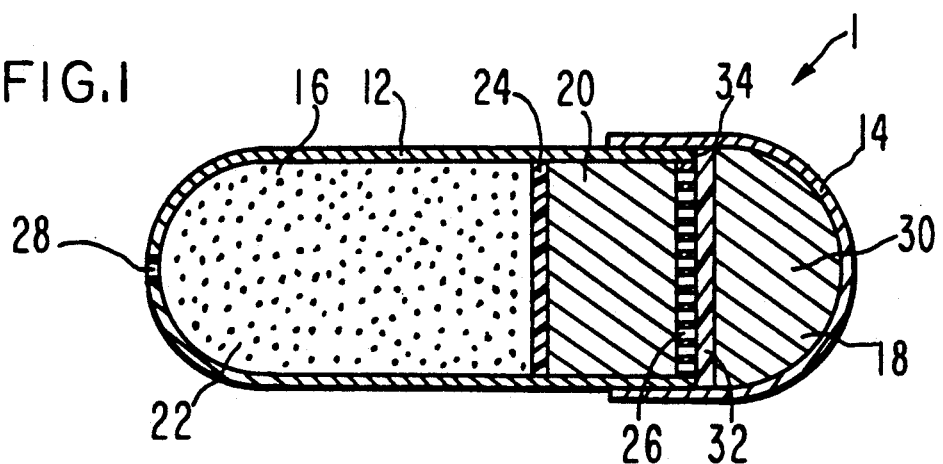
FIG. 1 is a cross-sectional view of one embodiment of the delivery device of the present invention, the device being in closed or prepared form prior to placement in the environment of use.

FIG. 1 depicts in cross-sectional view a presently preferred embodiment of the delivery device according to the present invention. The device is shown in closed or prepared form prior to placement in the environment of use. Dispensing device I comprises a first housing 12 and a second housing 14. First housing 12 and second housing 14 are in slidably telescoping arrangement with each other. First housing 12 surrounds and defines an active agent delivery chamber 16 and contains a first expansion means 20 and an active agent formulation 22, which in a preferred embodiment are separated by a moveable impermeable partition layer 24 to maintain the separate identities of the agent formulation 22 and the first expansion means 20. First housing 12 also comprises an exit means or passageway 28 which provides communication between the environment of use and that part of active agent delivery chamber 16 containing active agent formulation 22. Adjacent to first expansion means 20, on the side opposite from agent formulation 22, is fluid-passage means 26 for allowing the passage of fluid from the environment of use into expansion means 20.

Second housing 14 encompasses an expansion chamber 18 and contains a second expansion means 30 and a moveable impermeable push layer or push plate 32, push plate 32 being between second expansion means 30 and the end of first housing 12 that comprises the fluid-passage means 26.

First housing 12 and second housing 14 at their ends are close in size and they form a friction fit therebetween. The friction generated is sufficient to maintain the two housings together prior to activation of the second expansion means 30 but not so great as to keep the two housings from sliding apart once an expanding driving force is exerted. First housing 12 and second housing 14 can be telescoped completely into a closed and continuous external walled position. The end of first housing 12 is adapted to fit within second housing 14. The bottom edge of the end of first housing 12 provides a platform or ridge 34. Ridge 34 is adapted to receive the driving force of second expansion means 30, via push plate 32, to effect the separation of the two housings.

In operation, dispensing device 1 is placed in the fluid environment of use and second expansion means 30 begins to imbibe and absorb fluid through second housing 14 from the environment. Second expansion means 30 expands, exerting a driving force via push plate 32 against end or ridge 34 of first housing 12 to begin to slidably separate first housing 12 from second housing 14. At a point in time $t_a$, first housing 12 and second housing 14 are separated apart from each other by the action of second expansion means 30, via push plate 32, on first housing ridge 34. In such manner, fluid-passage means 26 is then exposed to the fluid environment, and prede-first expansion means 20 begins to imbibe fluid through fluid-passage means 26. As first expansion means 20 imbibes fluid, it expands and pushes against partition layer 24, and the expanding driving force of means 20 is conveyed via partition layer 24 against active agent formulation 22. Agent formulation 22 is then immediately begun to be expelled in a controlled and continuous manner from active agent delivery chamber 16 through exit port 28 into the environment of use. The expansion means 20 continues to expand and deliver active agent for a prolonged period of time, $t_b$.

Figure 2:
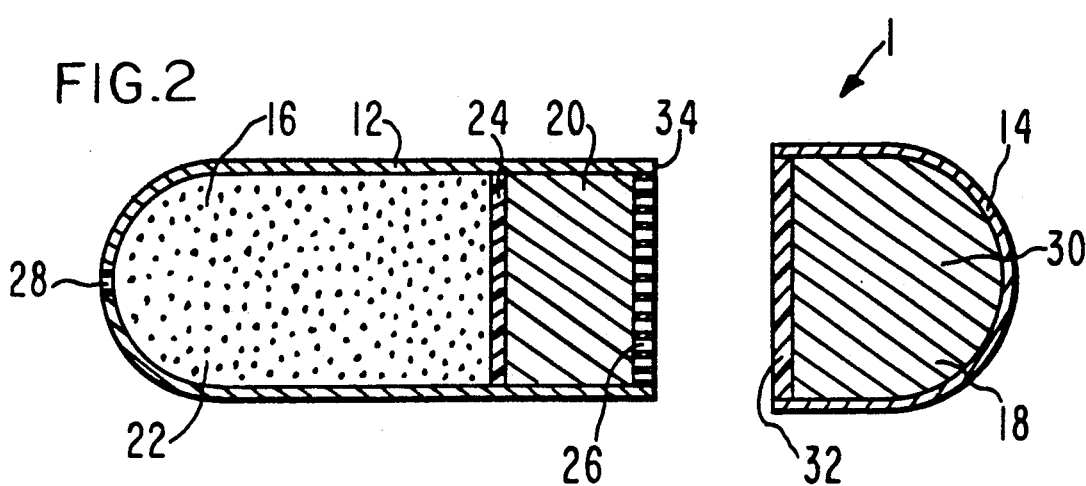
FIG. 2 shows the device of FIG. 1 in operation after placement in the environment of use, showing the second expansion means expanded and the first and second housings of the device separated to allow activation of the first expansion means to begin delivery of the active agent formulation to the environment.

FIG. 2 shows the dispensing device 1 of FIG. I in operation at time $t_a$ after separation of the two housings of the device by placement in the fluid environment. First housing 12 has been separated from second housing 14 by the expanding driving force of the second expansion means 30, which has expanded in size as a result of imbibing fluid from the environment. Fluid-passage means 26 is now exposed to the environment so that the device 1 is activated to begin to deliver active agent.

Figure 3:
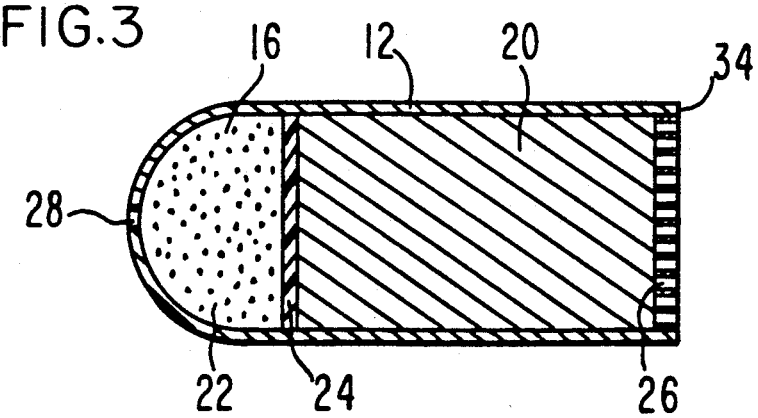
FIG. 3 shows the first housing of the device of FIG. 1 in operation toward the end of its useful life, with the first expansion means expanded and a large portion of the active agent formulation delivered to the environment.

FIG. 3 shows first housing 12 and the active agent delivery chamber 16 of dispensing device 1 of FIG. 1 in operation toward the end of the prolonged period of time $t_b$ after most of the active agent has been delivered to the environment. First expansion means 20 has expanded in size as a result of imbibing fluid through fluid-passage means 26 to push active agent formulation 22 through exit port 28.

FIG. 4 illustrates another embodiment of the device of the invention. As illustrated in this figure, dispensing device 2 is similar to dispensing device 1 of FIGS. 1 and 2, having a first housing 12 with a ridge 34, a second housing 14, an active agent delivery chamber 16 surrounded and defined by first housing 12, an expansion chamber 18 defined by second housing 14, first expansion means 20, second expansion means 30, push plate 32, and exit means 28. In dispensing device 2, the active agent formulation is present as a plurality of active agent dosage forms as layers or tablets 36, 38, 40 and 42. Although four dosage forms are illustrated, the number is not critical and any number of dosage forms are included under the invention. Optionally, layers of a barrier material (not shown) may be placed between the agent dosage forms in alternating arrangement to provide a pulsed delivery over a prolonged period of time. The exit means or passageway 28 may optionally be closed by an erodible material 44 such as, for example, microcrystalline wax or gelatin, for protecting the active agent formulation prior to placing in the environment of use, or there may optionally be present a retaining structure such as a screen or mesh for retaining the dosage forms within the device until they are dispensed into the environment. Alternately, a layer of barrier material (not shown) may be present between the first active agent dosage form and the environment of use at the exit means, which barrier layer is pushed out by the action of the activated first expansion means. Optionally, a partition layer (not shown), such as the partition layer 24 of device 1 in FIGS. 1, 2 and 3, may be included in device 2 between first expansion means 24 and dosage tablet 42.

Because first expansion means 20 operates by the imbibition of external fluid, the wall of first housing 12 is preferably comprised of an impermeable material in at least that portion of the housing that is in contact with the first expansion means 20, so that the first expansion means is not prematurely activated prior to the predetermined time $t_a$ of separation of the two housings of the device. When an active agent or an active agent dosage form is sensitive to fluid from an exterior fluid present in the environment of use, it is preferred that first housing 12 be substantially impermeable in its entirety to the ingress of the external fluid to serve as a means for substantially protecting the agent or dosage form as well as the first expansion means.

Because first expansion means 20 operates by the imbibition of external fluid, fluid-passage means 26 adjacent first expansion means 20 must allow fluid to pass through for activating the expansion means while being impermeable to the ingredients of the expansion means. This may be accomplished by the fluid-passage means comprising a microporous membrane or a screen or be of a composition that is semipermeable, or a combination of these. By "semipermeable" is meant that it is permeable to fluid but impermeable to other ingredients contained in the dispensing device.

FIG. 5 illustrates an embodiment where the fluid-passage means comprises a screen in combination with a semipermeable membrane. Device 3 of FIG. 5 has a first housing 12, a second housing 14, an active agent delivery chamber 16, an expansion chamber 18, a first expansion means 20, active agent formulation 22, a partition layer 24, a second expansion means 30, a push plate 32 and ridge 34. In device 3, the fluid-passage means comprises a screen 46 together with a semipermeable membrane 48. Screen 46 in this embodiment is molded or otherwise formed as a continuous portion of first housing 12. The screen 46 has openings or pores of such a size that components of first expansion means 20 could pass out into the environment of use, in addition to fluid passing into the expansion means. Thus, a semipermeable membrane 48 is positioned between screen 46 and first expansion means 20 to maintain the components of first expansion means 20 within device 3 while allowing fluid from the environment to pass through to means 20 via screen 46. In an optional embodiment of device 3, the push plate 32 is not present, since the continuous nature of the screen portion 46 of the housing 12 with the housing will, in certain embodiments, provide adequate support for the expanding driving force of the second expansion means 30. The end of first housing 12 opposite screen 46 and semipermeable membrane 48 is closed by a cap 50 having exit means or passageway 28 therethrough for enclosing the active agent delivery chamber 16. Cap 50 may be either semipermeable or impermeable, depending on the nature of the active agent formulation 22. Alternatively, exit means 28 may be of a large size such as that shown in FIG. 4, and optionally may be closed by an erodible material, by a barrier layer, or by a retaining structure such as a screen or mesh.

Because second expansion means 30 also operates by the imbibition of external fluid, the wall of second housing 14 in at least a portion that is adjacent to second expansion means 30 must be semipermeable.

The walls of housings 12 and 14 optionally comprise additional ingredients such as, for example, a plasticizer. Impermeable and semipermeable compositions suitable for use in housings 12 and 14, as well as suitable additives, are known in the art, examples of which are disclosed in U.S. Pat. No. 4,874,388, the entire disclosure of which is incorporated herein by reference.

The delivery device of the present invention is nontoxic, biologically inert, nonallergenic and nonirritating to body tissue, and it maintains its physical and chemical integrity; that is, the device does not erode or degrade in the environment of use during the dispensing period. It is within the scope of the invention that the device be insoluble only during the period of intended use and can thereafter dissolve away in the environment of use. Thus, a dispenser is here contemplated which is unaffected by its environment, solubility-wise, at the situs of use or which, alternatively, is only slightly soluble during the period of intended use, such that once its active agent content has been removed it will then dissolve or erode away.

The first and second expansion means or expandable driving means 20 and 30 are nontoxic, nonallergenic and biologically inert. Expansion means 20 and 30 may be the same or they may be different. In one presently preferred embodiment, means 20 and/or 30 comprises an osmopolymer. The osmopolymers interact with water and aqueous biological fluids and swell or expand to an equilibrium state. The osmopolymers exhibit the ability to swell in fluid and to retain a significant portion of the imbibed and absorbed fluid within the polymer structure. The expansion means 20 and/or 30 in another preferred embodiment comprises an osmagent. The osmagents are known also as osmotically effective solutes and they are also known as osmotically effective compounds. The osmagents that can be used for the purpose of this invention include inorganic and organic compounds that exhibit an osmotic pressure gradient across a semipermeable, i.e. a fluid-permeable, wall. The expansion means 20 and/or 30 in yet another preferred embodiment comprises an osmagent dispersed within an osmopolymer. The expansion means can comprise a tablet or a layer, or a plurality of tablets or layers, and be placed into position in the device or it can be pressed into the appropriate wall section. The osmagent or osmopolymer can be in any suitable form such as particles, crystals, pellets, granules, and the like, when pressed into a tablet layer and into the wall section. Osmagents and osmopolymers are known to the art and are described in, for example, U.S. Pat. Nos. 3,865,108, 4,002,173, 4,207,893, 4,327,725 and 4,612,008.

Partition layer 24 and push plate 32, in a presently preferred embodiment, each comprises a composition that is substantially impermeable to the passage of fluid, and they serve to restrict the passage of fluid present in the expansion means into other areas of the first or second housings. They operate to essentially maintain the integrity of the active agent formulation 22 or the fluid-passage means 26 and the expansion means layers. Additionally, and importantly, push plate 32 acts to insure that the expanding driving force generated by the second expansion means 30 is applied directly against first housing 12 to effect the separation of the first and second housings. Thus, push plate 32 must be of sufficient strength, thickness and rigidity to transfer the driving force against first housing 12.

Representative impermeable materials useful as a partition layer 24 or push plate 32 are known to the art in, for example, U.S. Pat. No. 4,874,388.

The term "active agent formulation", as used herein, comprises the active agent to be delivered, as a liquid, solid, semisolid or thermosensitive composition, generally in a carrier substance and with or without additional inert ingredients. The term may additionally include dosage forms comprising the active agent which are capable of maintaining their physical configuration and chemical integrity while housed within the dispenser. These include, without limitation, tablets with or without a density element; matrix tablets; spheres; pellets and elongated tablets; capsules; elementary osmotic pumps, such as those described in U.S. Pat. No.

3,845,770; mini-osmotic pumps, such as those described in U.S. Pat. Nos. 3,995,631, 4,034,756 and 4,111,202; and multichamber osmotic systems referred to as push-pull and push-melt osmotic pumps, such as those described in U.S. Pat. Nos. 4,320,759 and 4,449,983; all the above patents of which are incorporated herein by reference.

The pharmaceutically acceptable carrier useful herein may comprise more than one ingredient, such as, for example, a buffer, a viscosity regulating vehicle, a surfactant, dyes, a permeation enhancer, proteinase inhibitors, or other formulation ingredients and additives, as are known in the art. The carrier may contain more than one active agent. The active agent formulation can erode or disintegrate and can be in the form of a wax formulation, solid core or tablet, for example. The formulation can immediately dissolve upon exposure to fluid or it may erode slowly with or without the presence of excipients for controlling erosion.

The active agent formulation can be designed in a multitude of ways to provide a specific drug delivery profile. One embodiment may comprise a formulation that contains a biologically acceptable solid surfactant which is capable of slow dispersion in the environmental fluid. In another embodiment, the formulation may contain a fluid-insoluble wax and a surfactant so that the formulation is susceptable to erosion in the environment. In still another embodiment, the formulation may be effervescent and provide drug delivery in a finely dispersed form. This is accomplished by the addition of a solid basic compound capable of evolving carbon dioxide in the presence of an acid in the environment of use. Suitable basic compounds are disclosed in U.S. Pat. No. 4,265,874. In a further embodiment, the formulation may include an osmotic agent or solute, such as those described above with reference to the expansion means, so that when the formulation comes into contact with the environmental fluid, it immediately dissolves. In yet another embodiment, the agent formulation can be comprised of an agent and a thermoresponsive composition. In this manner, the formulation would exhibit solid-like properties at room temperature of 21° C. and within a few degrees Celsius thereof, and would have a melting point that approximates mammalian body temperatures of 37° C. and within a few degrees Celsius thereof. The term "thermoresponsive" as used herein in a preferred embodiment denotes the physical-chemical property of an agent carrier composition to exhibit solid, or solid-like properties at temperatures up to 31° C. and become fluid, semi-solid or viscous when disturbed by heat at temperatures from 31° C., usually in the range of 31° C. to 45° C. Suitable materials useful as active agent carriers and excipients are known in the art and are disclosed in U.S. Pat. Nos. 4,595,583 and 4,874,388, for example.

The terms "active agent" and "drug" are used interchangeably herein and refer to an agent, drug, compound, composition of matter or mixture thereof which provides some therapeutic, often beneficial, effect. This includes pesticides, herbicides, germicides, biocides, algicides, rodenticides, fungicides, insecticides, antioxidants, plant growth promoters, plant growth inhibitors, preservatives, antipreservatives, disinfectants, sterilization agents, catalysts, chemical reactants, fermentation agents, foods, food supplements, nutrients, cosmetics, drugs, vitamins, sex sterilants, fertility inhibitors, fertility promoters, microorganism attenuators and other agents that benefit the environment of use. As used herein, the terms further include any physiologically or pharmacologically active substance that produces a localized or systemic effect or effects in animals, including warm blooded mammals, humans and primates; avians; domestic household or farm animals such as cats, dogs, sheep, goats, cattle, horses and pigs; laboratory animals such as mice, rats and guinea pigs; fish; reptiles; zoo and wild animals; and the like. The active drug that can be delivered includes inorganic and organic compounds, including, without limitation, drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autocoid systems, the alimentary and excretory systems, the histamine system and the central nervous system. Suitable agents may be selected from, for example, proteins, enzymes, hormones, polynucleotides, nucleoproteins, polysaccharides, glycoproteins, M. lipoproteins, polypeptides, steroids, hypnotics and sedatives, psychic energizers, tranquilizers, anticonvulsants, muscle relaxants, antiparkinson agents, analgesics, antiinflammatories, local anesthetics, muscle contractants, antimicrobials, antimalarials, hormonal agents including contraceptives, sympathomimetrics, polypeptides and proteins capable of eliciting physiological effects, diuretics, lipid regulating agents, antiandrogenic agents, antiparasitics, neoplastics, antineoplastics, hypoglycemics, nutritional agents and supplements, growth supplements, fats, ophthalmics, antienteritis agents, electrolytes and diagnostic agents.

Examples of beneficial agents which this invention can be utilized with are prochlorperazine edisylate, ferrous sulfate, aminocaproic acid, mecaxylamine hydrochloride, procainamide hydrochloride, amphetamine sulfate, methamphetamine hydrochloride, benzphetamine hydrochloride, isoproteronol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, theophylline cholinate, cephalexin hydrochloride, diphenidol, meclizine hydrochloride, prochlorperazine maleate, phenoxybenzamine, thiethylperazine maleate, anisindone, diphenadione erythrityl tetranitrate, digoxin, isoflurophate, acetazolamide, methazolamide, bendroflumethiazide, chlorpropamide, tolazamide, chlormadinone acetate, phenaglycodol, allopurinol, aluminum aspirin, methotrexate, acetyl sulfisoxazole, erythromycin, hydrocortisone, hydrocorticosterone acetate, cortisone acetate, dexamethasone and its derivatives such as betamethasone, triamcinolone, methyltestosterone, 17-$\beta$-estradiol, ethinyl estradiol, ethinyl estradiol 3-methyl ether, pednisolone, 17-$\beta$-hydroxyprogesterone acetate, 19-norprogesterone, norgestrel, norethindrone, norethisterone, norethiederone, progesterone, norgesterone, norethynodrel, aspirin, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chlorpromazine, methyldopa, dihydroxyphenylalanine, theophylline, calcium gluconate, ketoprofen, ibuprofen, cephalexin, erythromycin, haloperidol, zomepirac, ferrous lactate, vincamine, diazepam, phenoxybenzamine, diltiazem, milrinone, captopril, mandol, quanbenz, hydrochlorothiazide, ranitidine, flurbiprofen, fenbufen, fluprofen, tolmetin, alclofenac, mefenamic, flufenamic, difuninal, nimodipine, nitrendipine, nisoldipine, nicardipine, felodipine, lidoflazine, tiapamil, gallopamil, amlodipine, mioflazine, lisinopril, enalapril, captopril, ramipril, enalaprilat, famotidine, nizatidine, sucralfate, etintidine, tetratolol, minoxidil, chlordiazepoxide, diazepam, amitriptylin, and imipramine. Further examples are proteins and peptides which include, but are not limited to, insulin, colchicine, glucagon, thyroid stimulating hormone, parathyroid and pituitary hormones, calcitonin, renin, prolactin, corticotrophin, thyrotropic hoemone, follicle stimulating hormone, chorionic gonadotropin; gonadotropin releasing hormone, bovine somatotropin, porcine somatropin, oxytocin, vasopressin, prolactin, somatostatin, lypressin, pancreozymin, luteinizing hormone, LHRH, interferons, interleukins, growth hormones such as human growth hormone, bovine growth hormone and porcine growth hormone, fertility inhibitors such as the prostaglandins, fertility promoters, growth factors, and human pancreas hormone releasing factor.

It is to be understood that more than one active agent may be incorporated into the active agent formulation in a device of this invention, and that the use of the term "agent" or "drug" in no way excludes the use of two or more such agents or drugs.

The agents can be in various forms, such as uncharged molecules, components of molecular complexes or nonirritating, pharmacologically acceptable salts. Also, simple derivatives of the agents (such as ethers, esters, amides, etc.) which are easily hydrolyzed by body pH, enzymes, etc., can be employed.

The amount of active agent employed in the delivery device will be that amount necessary to deliver a therapeutically effective amount of the agent to achieve the desired result at the site of delivery. In practice, this will vary widely depending upon the particular agent, the site of delivery, the severity of the condition, and the desired therapeutic effect. Thus, it is not practical to define a particular range for the therapeutically effective amount of active agent incorporated into the device.

As used herein, the terms "therapeutically effective" amount or rate refer to the amount or rate of the active agent needed to effect the desired therapeutic, often beneficial, result.

The terms "exit means" and "exit passageway", as used herein, comprise means and methods suitable for the metered release of the active agent formulation from agent delivery chamber 16 of the delivery device of the present invention. The exit means 28 includes at least one passageway, orifice, or the like, through first housing 12 for communicating with agent delivery chamber 16. The expression "at least one passageway" includes aperture, orifice, bore, pore, porous element through which the agent can migrate, hollow fiber, capillary tube, porous overlay, porous insert, and the like. The expression also includes material that is discharged, erodes or is leached from the wall of the first housing in the fluid environment of use to produce at least one passageway in the delivery device. Representative materials suitable for forming at least one passageway, or a multiplicity of passageways, include an erodible poly(glycolic) acid or poly(lactic) acid member in the wall; a gelatinous filament; poly(vinyl alcohol); leachable materials such as fluid-removable pore-forming polysaccharides, salts, or oxides; erodable or dischargable materials such as natural and synthetic waxes; and the like. The expression includes structural characteristics that concentrate stress at a precise point in the wall so that only a small amount of force will induce breakage in the wall, yielding a passageway through the wall from agent delivery chamber 16 to the outside of the device. A passageway or a plurality of passageways can be formed by leaching a material such as sorbitol, lactose and like water-soluble solids from the wall. A passageway or passageways can be formed by the discharge, as a result of the pressure created by the expandable driving means for example, of a material such as a wax. The exit means or passageway can have any shape such as round, triangular, square, elliptical, and the like, for assisting in the metered release of active agent from the delivery device. The delivery device can be constructed with one or more passageways in spaced-apart relations or more than a single surface of a dosage form. Passageways and equipment for forming passageways are disclosed in U.S. Pat. Nos. 3,845,770; 3,916,899; 4,063,064; and 4,088,864. Passageways formed by leaching are disclosed in U.S. Pat. Nos. 4,200,098 and 4,285,987.

The total delay time prior to separation of the two housings of the dispensing device and the total delivery time of the active agent formulation can be controlled by a number of means to provide a sharp start-up of delivery at a particular time with high accuracy. For example, the rate of fluid imbibition into each of the expansion means, and thus the rate of expansion of the means, can be controlled by the particular choice of semipermeable membrane or microporous screen. The rate of expansion of the expansion-means can also be controlled by the choice of composition of the expansion means. The distance of overlap between the telescoping portions of the first and second housings can determine the period of time required for the two housings to separate. Combinations of such control means may be used. Such control means are known in the art and can be determined without undue experimentation.

The delivery device of the present invention can be manufactured by standard manufacturing techniques. For example, in the preparation of devices of the present invention, first housing 12 (the vessel) and second housing 14 (the cap) may be separately molded or extruded to the desired shape. Possible semipermeable materials from which the second housing 14 may be prepared include, for example, Hytrel ® polyester elastomers (Du Pont), cellulose esters, water flux enhanced ethylene-vinyl acetate copolymers, semipermeable membranes made by blending a rigid polymer with water-soluble low molecular weight compounds, and other semipermeable materials known to the art. , Impermeable materials from which the first housing 12 may be prepared include, for example, polyethylene, polystyrene, ethylene-vinyl acetate copolymers, Hytrel ® polyester elastomers (Du Pont) and other impermeable materials known to the art. Alternatively, the two portions of a hard gelatin capsule may be coated, one with an impermeable material and the other with a semipermeable material such as cellulose ester-based polymer mixtures. In a presently preferred embodiment, the assembled device in closed configuration is about the size and dimensions of a size "0" to size "00" hard gelatin capsule. The exit means 28 may be formed during the molding process or may be drilled after the vessel portion has been made.

A "first bilayer osmotic plug" composed of impermeable partition layer 24 and first osmotic layer or expansion means 20 is prepared in a shape that will fit within vessel 12. The two layers are compressed into a tablet on a rotary bilayer tablet press.

A "second bilayer osmotic plug" composed of second osmotic layer or expansion means 30 and impermeable push plate 32 is prepared in a shape that will fit within cap 14. The osmotic plug is compressed on a bilayer rotary tablet press.

The device can be assembled by first placing a soluble seal or a hard gelatin cap over exit means 28 in vessel 12. Active agent formulation 22 is then placed in the vessel at its end opposite the exit means, which end is initially open; the formulation may be in the form of a liquid, solid, semisolid, powder or shaped tablet or tablets, for example. The first bilayer osmotic plug is then inserted on top of the agent formulation with the partition layer portion of the plug next to the agent fill, taking care that the least possible air gap exists between the agent fill and the first bilayer osmotic plug. Fluid-passage means 26 is then placed in vessel 12 in such manner that the final position of the passage means 26 is against the expansion means portion of the first osmotic plug and also is flush with the open end of the vessel. The fluid-passage means may be fixed into place (by adhesive bonding, ultrasound welding or mechanical fitting, for example). The second bilayer osmotic plug is placed within the cap 14 and the cap assembly is placed over the end of the filled vessel 14 so that push plate 32 is adjacent to fluid-passage means 26, to give a device as illustrated in FIG. 1. In an alternative assembly method, the device may be assembled as described above, but without addition of the active agent formulation. After assembly is completed, the device is oriented with the cap portion downwards and liquid or molten agent formulation is placed in the vessel portion through orifice 28. After filling, the open orifice may be sealed, if desired.

When the device of the invention has the configuration of FIG. 4, it may be prepared by molding or extruding a first housing or vessel 12 with two initially open ends. The fluid-passage means 26 is fitted flush to one end of the vessel cylinder and fixed within the cylinder (by adhesive bonding, ultrasound welding, or mechanical fitting, for example). The semipermeable second housing or cap 14 containing the second bilayer osmotic tablet (prepared as described above) is then placed over the passage means-containing end of the vessel. The first bilayer osmotic plug (as above) is inserted, expansion means layer first, through the other or drug delivery end of the vessel 12 and is placed flush with the fluid-passage means 26. The remainder of the vessel portion is then filled with active agent, typically in the form of one or more active agent tablets. The active agent tablets may optionally be separated by non-active agent-containing layers or tablets to provide a pulsed delivery of agent to the environment of use. After all agent formulation has been placed in the vessel, a cap 44, screen or other covering may be placed over the open end, if desired.

When the device of the invention has the configuration of FIG. 5, it may be prepared by molding or extruding a first housing or vessel 12 in the shape of a cup where the base of the cup has pores or other openings formed therein for the passage of fluid. This forms the screen portion 46 of the fluid-passage means. A semipermeable membrane 48 is then placed within the vessel 12 so that it is adjacent to the cup bottom or screen 46. The semipermeable second housing or cap 14 containing the second bilayer osmotic tablet (prepared as described above) is then placed over the screen end of the vessel. The first bilayer osmotic plug (as above) is inserted, expansion means layer first, through the open or drug delivery end of the vessel 12 and is placed flush with the semipermeable membrane 48. The remainder of the vessel portion is then filled with active agent, typically in the form of one or more active agent tablets. The active agent tablets may optionally be separated by non-active agent-containing layers or tablets to provide a pulsed delivery of agent to the environment of use. The active agent may alternatively be a fluid, solid, semi-solid or thermoresponsive material. After all agent formulation has been placed in the vessel, a cap 50 is placed over the open end. Exit means 28 may be formed when cap 50 is molded or otherwise made, or exit means 28 may be formed later by drilling, for example. Alternatively, it may be desirable, based on the content and/or form of the drug formulation or the intended release profile, to have no cap at all on the device, or to have a cap that dissolves or erodes after placement in the fluid environment, or to place a screen or other permeable retaining means over the open end of the vessel.

The following examples are illustrative of the present invention. They are not to be construed as a limitation of the scope of the invention. Variations and equivalents of these examples will be apparent to one skilled in the art in light of the present disclosure, the drawings and the claims herein.

EXAMPLE 1

A delivery device according to the present invention is prepared as follows.

The first osmotic engine portion of the device is a compressed bilayer tablet composed of 200 mg of a polymeric osmotic formulation (first expansion means) and a 50 mg wax-based partition layer.

The polymeric osmotic formulation has a composition of 59.5 wt % polyethylene oxide (Polyox ®️ 303, Union Carbine), 29 wt % sodium chloride, 5 wt % polyacrylic acid (Carbomer ®️ 934P, B.F. Goodrich), 5 wt % hydroxypropylmethylcellulose E-5 (Aqualon) and 1 wt % ferric oxide. During preparation, each of the above components is screened through a 40 mesh screen, and the sized components are added to a mixing vessel in the appropriate porportions. The dry components are mixed thoroughly for 10 minutes; then, ethanol is slowly added while mixing until a wet mass has formed. The wet mass is then screened through a 20 mesh screen, and the wet granules are allowed to air dry for 18 hours. After drying, the granules are passed once more through a 20 mesh screen. Magnesium stearate (0.5 wt %) is then added to the granulation and the granulation is mixed thoroughly for 5 min.

The partition layer has a composition of 95 wt % microcrystalline wax (MF-2JH Durawax ®️, Astor Wax Corp.) and 5 wt % gelatin (Type A, 250–300 bloom, Knox Gelatin). During preparation, each component is screened through a 40 mesh screen before being added in the correct weight ratio to a mixing vessel. The dry materials are then mixed thoroughly for 10 minutes, after which purified water is slowly added to the mixture while stirring is continued. After a wet mass has formed, the mixture is passed through a 20 mesh screen, and the granules are oven-dried at 40° C. for 24 hours. After the granules have dried, they are rescreened through a 20 mesh screen.

The osmotic formulation (200 mg) for the engine and the wax formulation (50 mg) for the partition layer are compressed together in a rotary press into a cylindrical bilayer tablet with both the osmotic engine face and the partition face of the tablet being flat. Tabletting is conducted to produce a clean, distinct interface between the two layers.

The second osmotic engine portion of the device is a compressed bilayer tablet composed of a 50 mg wax-based push plate and 150 mg of a polymeric osmotic formulation (second expansion means). The composition of the second osmotic formulation is the same as or can be different from that for the first osmotic formulation above, and the composition of the push plate is the same as that for the partition layer above. The osmotic formulation (150 mg) and the wax push plate formulation (50 mg) are compressed in a rotary press into a cylindrical bilayer tablet. The osmotic face of the tablet is convex, to conform to the shape of the device, while the push plate face of the tablet is flat. Tabletting was conducted to produce a clean, distinct interface between the two layers.

The vessel portion (first housing) of the device, with one closed and one open end, is composed of polyethylene and is prepared by placing the polyethylene in an extruder with a barrel temperature of 130° C. and extruding the material into a mold for the vessel. The polyethylene is allowed to cool in the mold, after which the finished vessel is removed. An exit orifice is drilled through the closed end of the vessel.

To prepare the cap portion (second housing) of the device, 70 wt % cellulose acetate 320 and 30 wt % polypropylene glycol are thoroughly mixed together and the mixture is added to the hopper of a screw extruder. The polymeric mixture is heated at 127° C. as it is extruded through the heated barrel of the extruder and is extruded into a mold for the cap. The polymer mixture is allowed to cool after injection into the mold, after which the cap is removed.

The fluid-passage means is formed as a screen with fine openings and is composed of the same polymeric material as the vessel portion. After heating, the polyethylene is molded into a disk shape (with an outside diameter equal to the inside diameter of the vessel at its open end) with fine openings extending through it. Alternatively, the fluid-passage means is formed as a macroporous plug made by sintering together polymeric particles of high density polyethylene or polypropylene (marketed as Porex ®), the plug having an outside diameter equal to the inside diameter of the vessel at its open end.

To assemble the delivery device, a first osmotic engine bilayer tablet is placed into the vessel, with the partition layer portion of the tablet facing into the vessel. A fluid-passage screen or plug is then placed into the vessel, flush with the bilayer tablet and also flush with the open end of the vessel. The screen or plug is secured in place by ultrasound welding. The vessel is then turned over and the desired active agent formulation is placed into the vessel through the exit orifice by manual or automated fill mechanisms. The exit orifice is then sealed with a wax having a melting point of about 34° C., by dipping the exit end of the vessel in the melted wax and allowing it to cool for about 20 seconds, after which the excess wax is wiped off. Next, a second osmotic engine bilayer tablet is placed into a completed cap, with the convex osmotic layer pointed into the closed end of the cap and the push plate exposed toward the cap opening. The open end of the filled vessel is fitted inside the open end of the cap, and the two pieces are compressed together until cap, second osmotic bilayer tablet and vessel fit together tightly. When the delivery device is placed in an environment at 37° C. (e.g., the body temperature of a human), the wax sealing the exit orifice is melted away to allow delivery of active agent.

EXAMPLE 2

Another embodiment of a delivery device according to the present invention is prepared as follows.

A first osmotic engine portion is prepared as described in Example 1.

A second osmotic engine portion is prepared substantially as described in Example 1, except that the second osmotic portion does not include a push plate but comprises only 150 mg of the polymeric osmotic formulation pressed into a monolayer tablet having a convex face and a flat face.

The vessel portion (first housing) of the device, composed of lo polyethylene, is extruded following the procedures of Example 1 into a mold. The resulting vessel has one open and one closed end, the closed end being flat and having a plurality of openings molded into it to form the screen portion of the fluid-passage means.

The semipermeable membrane portion of the fluid-passage means is formed as a semipermeable membrane and is composed of the same polymeric material as the first cap portion, below. After heating, the polymeric mixture is extruded as a sheet and, after cooling of the sheet, a circle or disk having the same diameter as the inside diameter of the vessel portion at its closed end is punched out of the sheet to make the semipermeable membrane disk.

The first cap portion (second housing) of the device is prepared by melt-blending together 60 wt % ethylene vinyl acetate (with 9% vinyl acetate content) and 40 wt % polyvinyl pyrrolidone at 110° C. and injection-molding or extruding the mixture into a mold for the cap. The polymer mixture is allowed to cool after injection, after which the cap is removed from the mold.

The second cap portion is made by extruding ethylene vinyl acetate (9% vinyl acetate content) into a mold for a cap to fit over the open end of the vessel portion. After the finished second cap is removed from the mold, an exit orifice is drilled through the cap.

To assemble the delivery device, the semipermeable membrane disk is placed into the vessel through its open end and situated against its closed end. The first osmotic engine bilayer tablet is placed into the vessel, with the osmotic layer portion of the tablet in contact with the semipermeable membrane. The desired active agent formulation is then placed into the vessel by manual or automated fill mechanisms. The vessel is then closed by placing the second cap with the exit orifice over the open end of the vessel. The cap is secured in place by adhesive seal. Next, the second osmotic engine monolayer tablet is placed into a completed first cap, with the convex face of the tablet pointed into the closed end of the cap. The flat, screen end of the vessel is fitted inside the open end of the first cap, and the two pieces are compressed together until cap, second osmotic layer and vessel fit together tightly.

EXAMPLE 3

A further embodiment of the delivery device of the present invention is prepared following the procedures of Example 2, except that the second cap portion is comprised of gelatin, which will erode when placed in a fluid environment. No exit orifice is drilled in this second cap. The active agent formulation is comprised of a plurality of individual tablets which are placed longitudinally within the vessel portion. The active agent tablets are separated by non-active agent-containing layers having the same composition as the partition layer.

The above description has been given for ease of understanding only. No unnecessary limitations should be understood therefrom, as modifications will be obvious to those skilled in the art.

What is claimed is:

1. A fluid-imbibing delivery device for dispensing an active agent to a fluid environment of use over a predetermined prolonged period of time of from about 1 hour to about 48 hours after an initial, preset delayed startup of delivery, which device maintains its integrity in the fluid environment, wherein the device comprises:
   (a) a first housing and a second housing, the first and second housings being in reversibly sliding telescoping arrangement with each other, the first housing being impermeable in at least a portion and having an end adapted to fit within the second housing and the second housing being semipermeable in at least a portion;
   (b) an active agent delivery chamber within the first housing comprising
      (i) at least one active agent formulation,
      (ii) a first fluid-activated expansion means selected from osmagents, osmopolymers or mixtures of osmagents with osmopolymers for expelling the active agent formulation from the delivery device,
      (iii) an exit means, and
      (iv) a fluid-passage means selected from the group consisting of a screen, a microporous membrane, a semipermeable composition and combinations of these; and
   (c) an expansion chamber within the second housing, the expansion chamber comprising
      (i) a second fluid-activated expansion means selected from osmagents, osmopolymers or mixtures of osmagents with osmopolymers for separating apart the first and second housings, and
      (ii) a push plate adjacent the telescoping end of the first housing.

2. A delivery device according to claim 1 which further comprises a partition layer between the active agent formulation and the first expansion means.

3. A delivery device according to claim 1 wherein the first housing is comprised of an impermeable material and the second housing is comprised of a semipermeable material.

4. A delivery device according to claim 1 wherein the active agent formulation is a liquid, a solid, a semi-solid, a thermoresponsive composition or a plurality of dosage forms.

5. A method for delivering an active agent to a fluid environment of use for a predetermined prolonged period of time of from about 1 hour to about 48 hours after an initial delayed startup of delivery, the method comprising:
   (1) placing a fluid-imbibing delivery device into the fluid environment, which device maintains its integrity in the fluid environment, wherein the delivery device comprises:
      (a) a first housing and a second housing, the first and second housings being in reversibly sliding telescoping arrangement with each other, the first housing being impermeable in at least a portion and having an end adapted to fit within the second housing and the second housing being semipermeable in at least a portion;
      (b) an active agent delivery chamber within the first housing comprising
         (i) at least one active agent formulation,
         (ii) a first fluid-activated expansion means selected from osmagents, osmopolymers or mixtures of osmagents with osmopolymers for expelling the active agent formulation from the delivery device,
         (iii) an exit means, and
         (iv) a fluid-passage means selected from the group consisting of a screen, a microporous membrane, a semipermeable composition and combinations of these; and
      (c) an expansion chamber within the second housing, the expansion chamber comprising
         (i) a second fluid-activated expansion means selected from osmagents, osmopolymers or mixtures of osmagents with osmopolymers for separating apart the first and second housings, and
         (ii) a push plate adjacent the telescoping end of the first housing;
   (2) allowing fluid to be imbibed through at least a portion of the second housing of the delivery device for causing the second expansion means to expand and exert pressure on the slidably connected first and second housings to push apart and separate the two housings to expose the fluid-passage means to the environment; and
   (3) allowing fluid to be imbibed through the fluid-passage means for causing the first expansion means to expand to push the active agent formulation from the delivery device.

6. A method according to claim 5 wherein the delivery device further comprises a partition layer between the active agent formulation and the first expansion means.

7. A method according to claim 5 wherein the first housing is comprised of an impermeable material and the second housing is comprised of a semipermeable composition.

8. A method according to claim 5 wherein the active agent formulation is a liquid, a solid, a semisolid, a thermoresponsive composition or a plurality of dosage forms.

9. A fluid-imbibing delivery device for dispensing an active agent in a pulsatile manner to a fluid environment of use over a predetermined prolonged period of time of from about 1 hour to about 48 hours after an initial, preset delayed startup of delivery, which device maintains its integrity in the fluid environment, wherein the device comprises:
   (a) a first housing and a second housing, the first and second housings being in reversibly sliding telescoping arrangement with each other, the first housing being impermeable in at least a portion and having an end adapted to fit within the second housing and the second housing being semipermeable in at least a portion;
   (b) an active agent delivery chamber within the first housing comprising (i) a plurality of active agent layers containing at least one active agent longitudinally disposed with the active agent delivery chamber, the active agent layers being separated by non-active agent-containing layers, (ii) a first fluid-activated expansion means selected from osmagents, osmopolymers or mixtures of osmagents with osmopolymers for expelling the active agent layers from the delivery device, (iii) an exit means, and (iv) a fluid-passage means selected from the group consisting of a screen, a microporous membrane, a semipermeable composition and combinations of these; and (c) an expansion chamber within the second housing, the expansion chamber comprising (i) a second fluid-activated expansion means selected from osmagents, osmopolymers of mixtures of osmagents with osmopolymers for separating apart the first and second housings, and (ii) a push plate adjacent the telescoping end of the first housing.

10. A delivery device according to claim 9 which further comprises a partition layer between the active agent layers and the first expansion means.

11. A delivery device according to claim 9 wherein the exit means is closed by an erodible material.

12. A delivery device according to claim 9 which further comprises a retaining structure across the exit means.

13. A method for delivering an active agent in a pulsatile manner to a fluid environment for use for a predetermined prolonged period of time of from about 1 hour to about 48 hours after an initial delayed startup of delivery, the method comprising:

(1) placing a fluid-imbibing delivery device into the fluid environment, which device maintains its integrity in the fluid environment, wherein the delivery device comprises:

(a) a first housing and a second housing, the first and second housings being in reversibly sliding telescoping arrangement with each other, the first housing being impermeable in at least a portion and having an end adapted to fit within the second housing and the second housing being semipermeable in at least a portion;

(b) an active agent delivery chamber within the first housing comprising (i) a plurality of active agent layers containing at least one active agent longitudinally disposed with the active agent delivery chamber, the active agent layers being separated by non-active agent-containing layers.

(ii) a first fluid-activated expansion means selected from osmagents, osmopolymers or mixtures of osmagents with osmopolymers for expelling the active agent layers from the delivery device, (iii) an exit means, and (iv) a fluid-passage means selected from the group consisting of a screen, a microporous membrane, a semipermeable composition and combinations of these; and (c) an expansion chamber within the second housing, the expansion chamber comprising (i) a second fluid-activated expansion means selected from osmagents, osmopolymers or mixtures of osmagents with osmopolymers for separating apart the first and second housings, and (ii) a push plate adjacent the telescoping end of the first housing;

(2) allowing fluid to be imbibed through at least a portion of the second housing of the delivery device for causing the second expansion means to expand and exert pressure on the slidably connected first and second housings to push apart and separate the two housing to expose the fluid-passage means to the environment; and (3) allowing fluid to be imbibed through the fluid-passage means for causing the first expansion means to expand to push the active agent layers and the non-active agent-containing layers sequentially from the delivery device.

14. A method according to claim 13 which further comprises a partition layer between the active agent layers and the first expansion means.

15. A method according to claim 13 wherein the exit means is closed by an erodible material.

16. A method according to claim 13 which further comprises a retaining structure across the exit means.

* * * * *